United States Patent [19]
Cho et al.

[11] Patent Number: 5,369,807
[45] Date of Patent: Dec. 6, 1994

[54] THERAPEUTIC GLOVE

[76] Inventors: Kurt N. Cho; Chae H. Cho, both of 13411 Ascot Glen, Houston, Tex. 77082

[21] Appl. No.: 32,687

[22] Filed: Mar. 17, 1993

[51] Int. Cl.5 .............................................. A41D 19/00
[52] U.S. Cl. ...................................... 2/159; 2/161.7; 2/162; 607/111
[58] Field of Search ..................... 2/159, 160, DIG. 3, 2/DIG. 7, 162, 158, 161.7, 168, 16; 607/108, 111; 128/DIG. 20; 602/2, 21

[56] References Cited

U.S. PATENT DOCUMENTS

| | | | |
|---|---|---|---|
| 2,582,648 | 1/1952 | Mowbray | 128/DIG. 20 |
| 2,792,827 | 5/1957 | Gravin et al. | 2/159 |
| 3,785,374 | 1/1974 | Lipson | 128/DIG. 20 |
| 3,869,594 | 3/1975 | Shively | 607/111 |
| 4,168,063 | 9/1979 | Rowland | 128/DIG. 20 |
| 4,281,647 | 8/1981 | Antypas | 602/21 |
| 4,587,672 | 5/1986 | Madnick et al. | 2/159 |
| 4,628,918 | 12/1986 | Johnson, Jr. | 128/DIG. 20 |
| 4,759,084 | 7/1988 | Madnick et al. | 2/160 |
| 4,781,189 | 11/1988 | Vijil-Rosales | 128/DIG. 20 |
| 5,025,502 | 6/1991 | Raymond et al. | 2/159 |
| 5,035,003 | 7/1991 | Rinehart | 2/159 |
| 5,062,414 | 11/1991 | Grim | 128/DIG. 20 |
| 5,088,478 | 2/1992 | Grim | 128/DIG. 20 |
| 5,155,864 | 10/1992 | Walker et al. | 2/DIG. 3 |

FOREIGN PATENT DOCUMENTS

| | | | |
|---|---|---|---|
| 1260201 | 9/1989 | Canada | 2/168 |
| 3027061 | 3/1982 | Germany | 2/159 |
| 9217079 | 10/1992 | WIPO | 2/159 |

Primary Examiner—Clifford D. Crowder
Assistant Examiner—Amy B. Vanatta

[57] ABSTRACT

A therapeutic glove that may be used to provide pressure and heat to relieve pain caused from arthritis or other ailments in a user's hand. The glove utilizes a heat retaining gel that may be warmed with hot water and the like to provide therapeutic heat to the hand of a user over a period of time. To provide for further therapy, the glove includes a small air pump that may be used to inject air into the glove to provide pain relieving pressure on the user's hand.

1 Claim, 4 Drawing Sheets

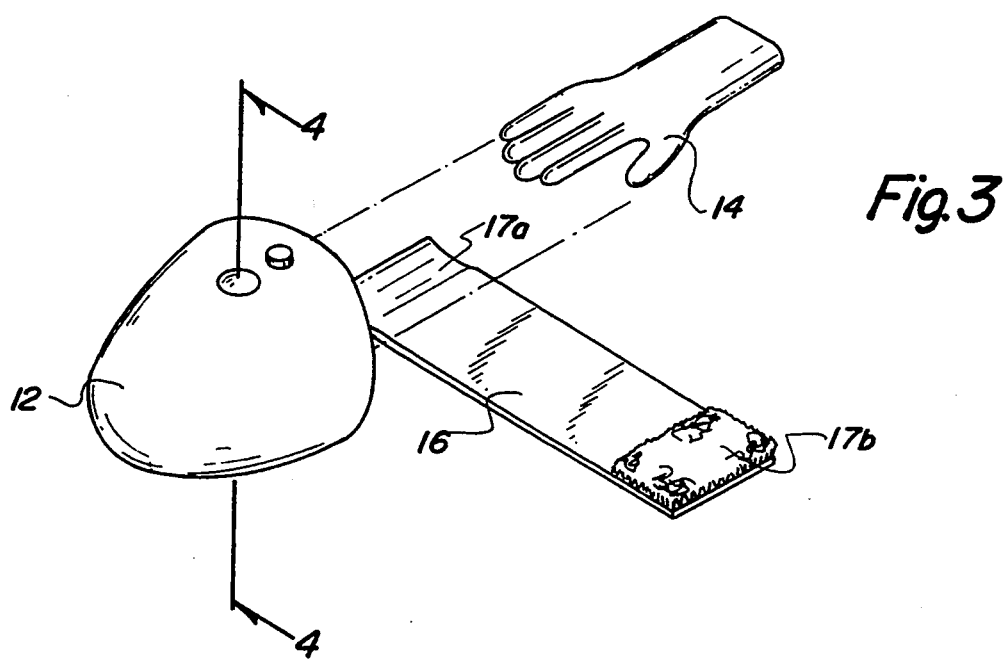
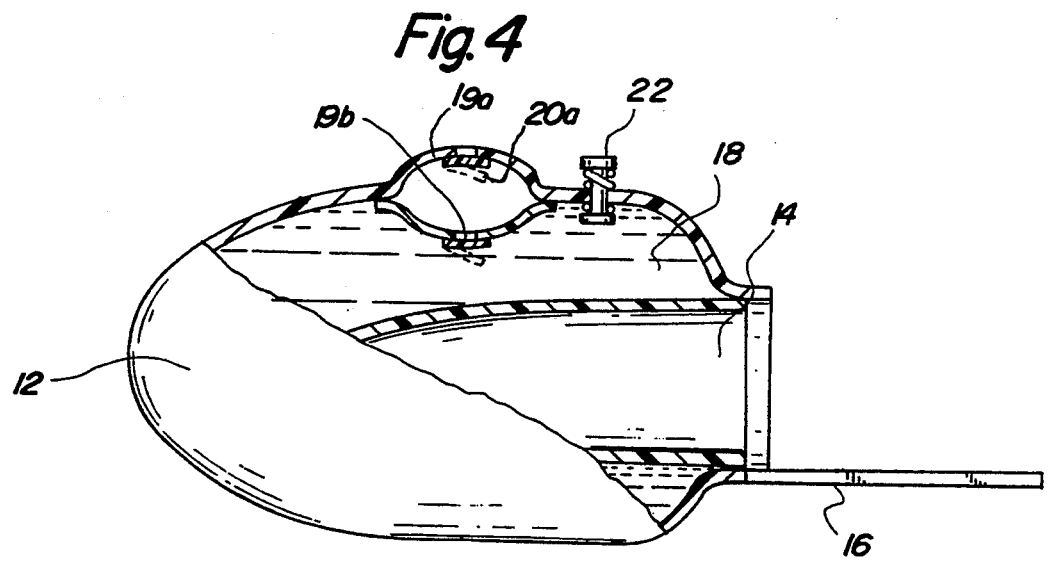

THERAPEUTIC GLOVE

BACKGROUND OF THE INVENTION

1. Field of the Invention

The present invention relates to therapeutic gloves and more particularly pertains to therapeutic gloves which may be used to provide heat and pressure to relieve hand pain in those people with arthritic hands and similar conditions.

2. Description of the Prior Art

The use of a therapeutic heated glove is known in the prior art. More specifically, gloves heretofore devised and utilized for the purpose of warming hands are known to consist basically of familiar, expected and obvious structural configurations, notwithstanding the myriad of designs encompassed by the crowded prior art which have been developed for the fulfillment of countless objectives and requirements.

For example, U.S. Pat. No. 5,035,003, which issued to Rinehart on Jul. 30, 1991, discloses a liquid heat transfer glove which includes a partially filled bladder of a heat-transferring liquid, whereby a user's hand may be comfortable in extreme temperature conditions.

A pressure glove for use in low atmospheric pressure conditions is described in U.S. Pat. No. 3,801,988 which issued to Marcum, Jr. et al. This device provides for an increase in the pressure around a user's hand when abnormal atmospheric pressure conditions are encountered.

U.S. Pat. No. 4,950,868, which issued to Moss, et al. on Aug. 21, 1990, discloses a heated glove which includes a battery pack mounted on the back of the glove.

None of the above mentioned patents discloses a glove which provides pressure as well as heat treatment to provide therapeutic relief to the hand of the wearer.

In this respect, the glove according to the present invention substantially departs from the conventional concepts and designs of the prior art, and in so doing provides an apparatus primarily developed for the purpose of providing relief from hand pain to those persons with arthritic hands and similar conditions.

Therefore, it can be appreciated that there exists a continuing need for new and improved therapeutic gloves which can be used to ease pain in a user's hand. In this regard, the present invention substantially fulfills this need.

SUMMARY OF THE INVENTION

In view of the foregoing disadvantages inherent in the known types of gloves now present in the prior art, the present invention provides an improved therapeutic glove which will help ease the pain in the hands of users' with arthritis and similar conditions. As such, the general purpose of the present invention, which will be described subsequently in greater detail, is to provide a new therapeutic glove which has many of the advantages of the gloves mentioned heretofore and many novel features that result in a glove which is not anticipated, rendered obvious, suggested, or even implied by any of the prior art gloves, either alone or in any combination thereof.

To attain this, the present invention essentially comprises an outer shell enclosing an elastic glove while providing ample space for a heat retaining gel to reside between the elastic glove and the outer shell. The heat retaining gel may then be heated by cascading hot water over the outer shell thereby heating the heat retaining gel therein. The glove may then be secured to a user's hand by a wrist strap to provide a continuous flow of pain relieving heat to the user's hand.

To further the therapeutic effects of the glove, a small pump is secured to the outer shell to facilitate the injection of air into the space occupied by the heat retaining gel between the outer shell and the elastic glove. The injection of air into the glove provides a pain relieving therapeutic pressure upon the user's hand. To decrease the pressure after use, an air release valve is also secured to the outer shell.

A second embodiment of the invention includes all of the foregoing features as well as an inflatable air bladder in the wrist strap that may be used to releaseably seal the user's wrist within the device. The wrist strap air bladder circumscribes the user's wrist and is inflatable with a small air pump which is secured to the wrist band in a well understood manner. A valve is provided in the wrist band to release the air contained within the wrist strap after use.

A further embodiment of the invention includes all of the foregoing features as well as protective caps that cover the relief valves to prevent the accidental action of the relief valves during any activity undertaken by the user.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic glove which has many of the advantages of the gloves mentioned heretofore and many novel features that result in a glove which is not anticipated, rendered obvious, suggested, or even implied by any of the prior art either alone or in any combination thereof.

It is another object of the present invention to provide a new therapeutic glove which may be easily and efficiently manufactured and marketed.

It is a further object of the present invention to provide a new therapeutic glove which is of a durable and reliable construction.

An even further object of the present invention is to provide a new therapeutic glove which is susceptible of a low cost of manufacture with regard to both materials and labor, and which accordingly is then susceptible of low prices of sale to the consuming public, thereby making such therapeutic gloves economically available to the buying public.

Still yet another object of the present invention is to provide a new therapeutic glove which provides in the apparatuses and methods of the prior art some of the advantages thereof, while simultaneously overcoming some of the disadvantages normally associated therewith.

Still another object of the present invention is to provide a new therapeutic glove that is capable of storing heat for release upon a user's hand to provide therapeutic relief of arthritis and similar conditions.

Yet another object of the present invention is to provide a new therapeutic glove which creates pressure upon the user's hand to provide therapeutic relief of arthritis and similar conditions.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an exploded view of the invention.

FIG. 4 is a cross sectional view taken along line 4—4 of FIG. 3.

DESCRIPTION OF THE PREFERRED EMBODIMENT

Figure 1:
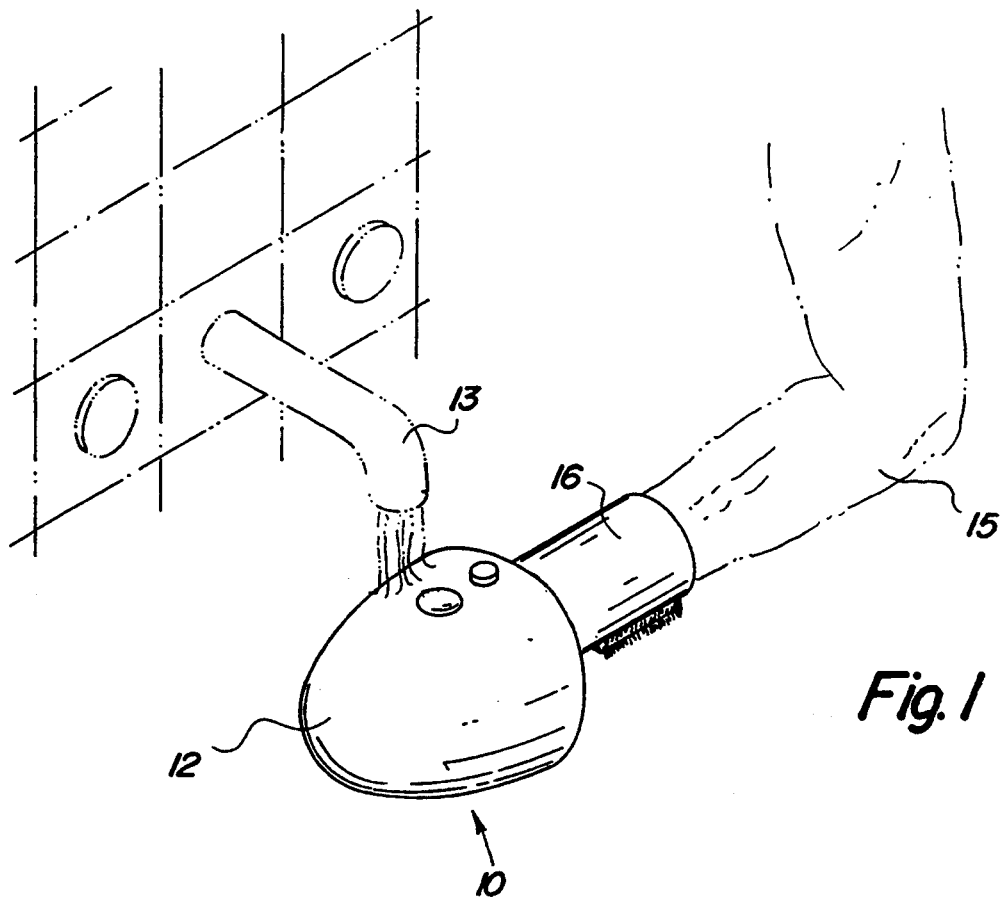
FIG. 1 is a perspective view of the glove comprising the present invention as it is being worn by a user and being heated by hot tap water.
Figure 2:
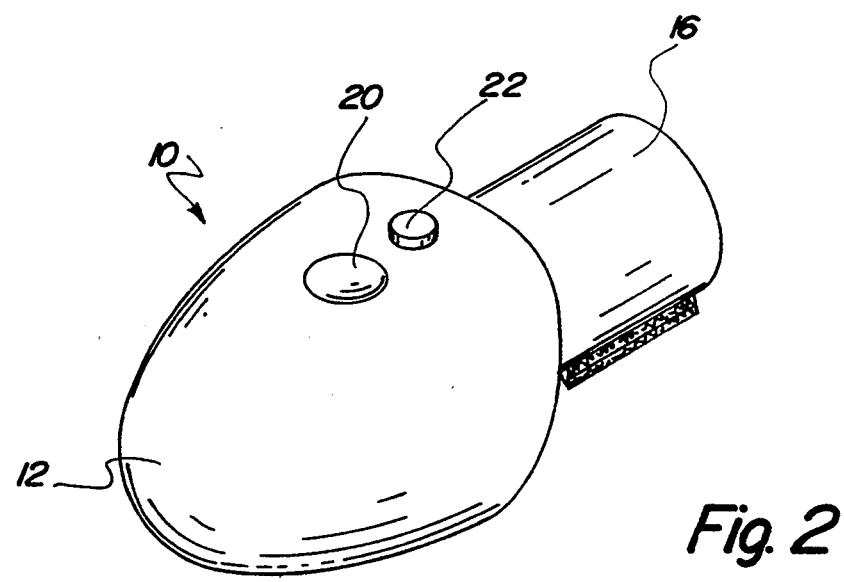
FIG. 2 is a further perspective view of the glove comprising the present invention.

With reference now to the drawings, and in particular to FIGS. 1-3 thereof, a first embodiment of a new therapeutic glove embodying the principles and concepts of the present invention and generally designated by the reference numeral 10 will be described.

More particularly, it will be noted that the first embodiment 10 of the invention comprises an outer shell 12 sized to receive and completely encompass an elastic glove 14. The elastic glove 14 is attached at the wrist area by some conventional means both to the outer shell 12 and to a wrist strap 16. The wrist strap 16 may then be secured by engaging the hook material 18 on the wrist strap to accompanying loop material (not shown) in a well understood manner to secure the therapeutic glove 10 to a user 20 as best illustrated in FIGS. 1 and 3.

In detail and referring to FIG. 4, it will be shown that the invention 10 further comprises a heat retaining gel 22 residing between the outer shell 12 and the elastic glove 14 to provide heat storage for release upon a user's hand (not shown) when inserted into the glove. The outer shell 12 is further equipped with a pump 24 which is secured to the outer shell in a conventional manner so that air may be pumped into the space 26 occupied by the gel 22 to create pressure upon a user's hand. The pump 24 is essentially comprised of a flexible diaphragm 28 attached to the outer shell 12 and formed in such a manner so as to define an aperture 30 through which air may pass. The aperture 30 is equipped with a valve 32 that is attached in a conventional manner so as to facilitate the single direction passing of air through the aperture. The pump 24 is further comprised of a back plate 34 formed in such a manner so as to define a further aperture 36 through which air may pass. The aperture 36 is also equipped with a further one way air valve 38 that facilitates the single direction passing of air through this the aperture. As shown, the pump 24 may be selectively operated to inject air into the space 26 occupied by the gel 22 to increase the pressure upon a user's hand when inserted into the glove 14.

To facilitate a release of the air injected into the invention 10 by the pump 24, a relief valve 40 is operably attached to the outer shell 12 so that air under pressure residing in the space 26 occupied by the heat retaining gel 22 will be biased out of the outer shell and into the atmosphere. The relief valve 40 essentially comprises a valve body 42 equipped with a seal 44 and a spring 46 to bias the valve body against the outer shell 12 whereby fluid communication between the space 26 occupied by the gel 22 and the atmosphere is releaseably blocked by the seal, the valve being operable to release the air contained therein. The seal 44 is lubricated by the gel 22 to maintain an effective block of possible fluid communication between the space 26 occupied by the gel 22 and the atmosphere.

Figure 5:
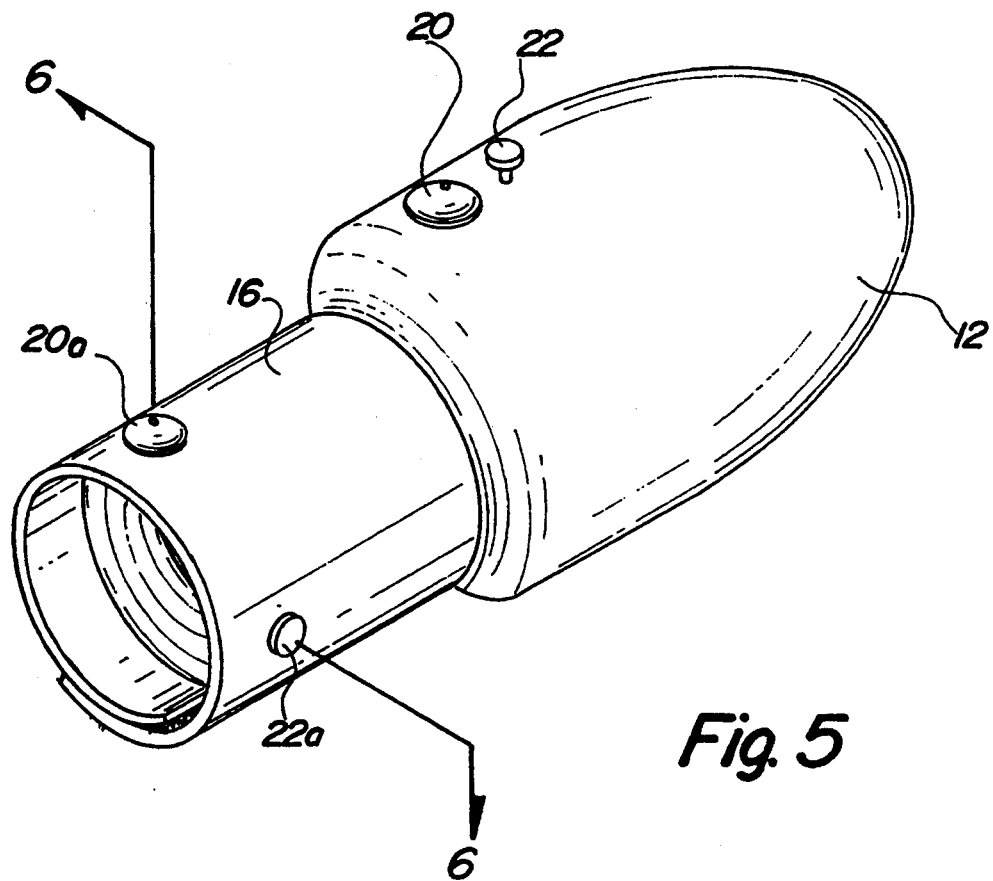
FIG. 5 is a perspective view of a second embodiment of the invention.
Figure 6:
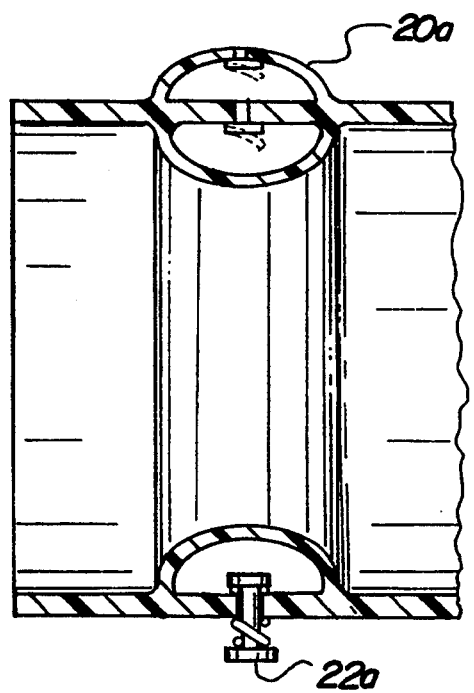
FIG. 6 is a cross sectional view taken on line 6—6 of FIG. 5.

A second embodiment of the invention, which is generally designated by the reference numeral 11 and is best shown in FIGS. 5 and 6, comprises all of the foregoing mentioned features of the first embodiment 10 and further comprises an additional pump 48 attached to the wrist strap 16 and an internal air bladder 50 to receive air injected by the pump whereby the invention may be releaseably sealed to the user's hand in a readily apparent manner. The pump 48 comprises a further flexible diaphragm 52 attached to the wrist strap 16 and formed in such a manner so as to define an aperture 54 through which air may pass, with this the aperture being equipped with a valve 56 that facilitates the single direction passing of air through the aperture. The pump 48 is further comprised of a portion of the wrist strap 16 which may be used as a back plate 58 and is formed in such a manner so as to define a further aperture 60 through which air may pass. The further aperture 60 is also equipped with a further valve 62 that facilitates the single direction passing of air therethrough. The pump 48 may be operated to inject air into the air bladder 50 to releaseably seal a user's hand inside the invention 11. The wrist strap 16 is also equipped with a further relief valve 64 to release the air inside of the air bladder 50 that is similar in construction and operation to the relief valve 40 present on the outer shell 12.

Figure 7:
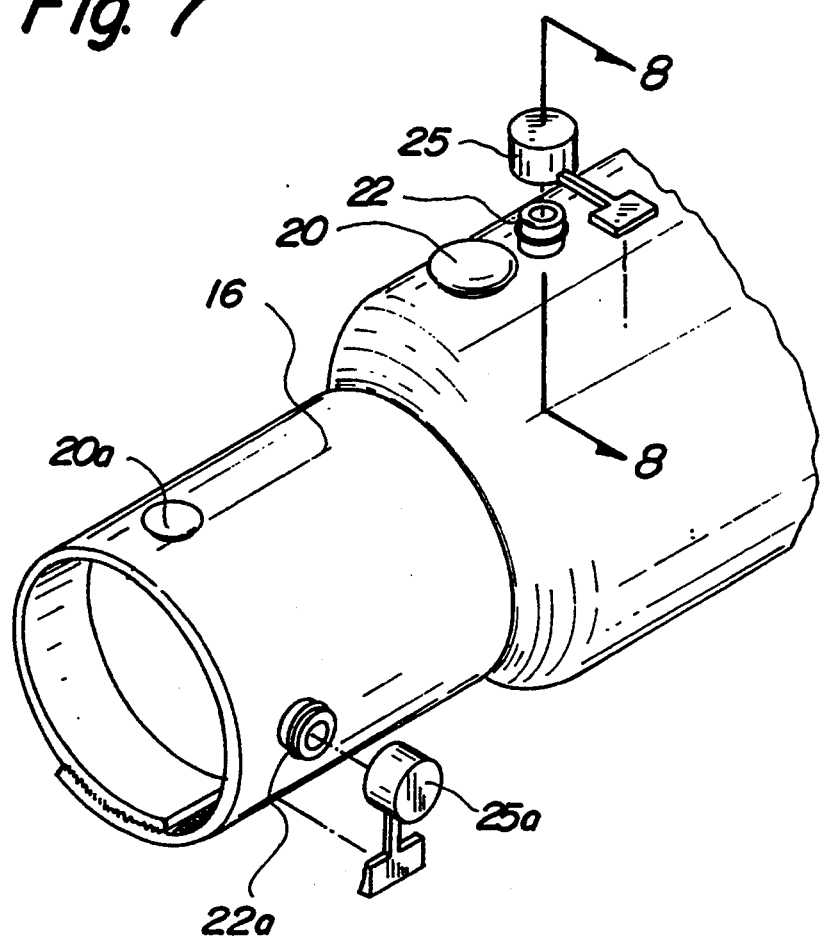
FIG. 7 is a partially exploded view of the glove shown in FIG. 5.
Figure 8:
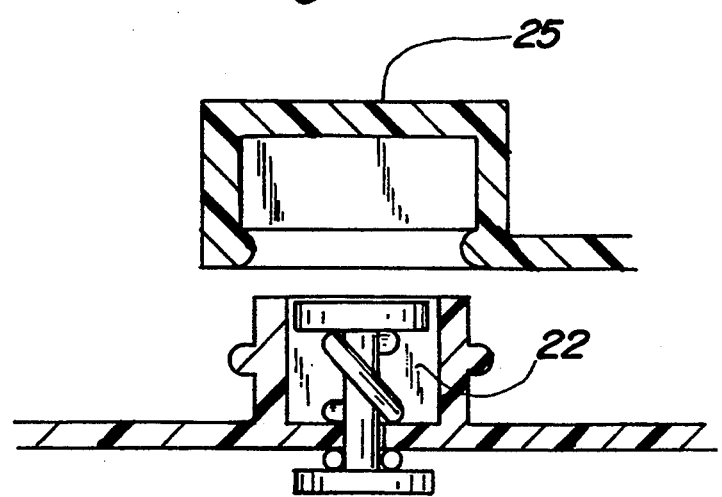
FIG. 8 is a partial cross sectional view taken on line 8—8 of FIG. 7.

A further embodiment of the invention 13, as can be seen in FIGS. 7 and 8, comprises all of the foregoing features and further comprises protective caps 66, 68 that may be respectively engaged to valve guards 70, 72 to cover relief valves 40 and 64, respectively, thereby to prevent the accidental actuation of the relief valves during any activity undertaken by the user.

An accepted treatment for sore hand conditions is heat and pressure. The therapeutic glove of the present invention creates a pressure upon the user's hand, which provides a massaging effect, while the gel retains heat to provide for a therapeutic warming of the user's hand.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Such modifications are intended to include a use of the invention in a therapeutic capacity on any conceivable portion of the human body, with the intent and purview of the invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A therapeutic glove comprising:

a glove for covering a hand of a user;

an outer shell to receive and substantially cover said glove to form a space between an inside surface of said outer shell and an outside surface of said glove;

a heat retaining gel present in said space for heating said glove;

a first pumping means for injecting air into said space, said first pumping means comprising a flexible diaphragm having a first aperture and being integrally formed with and sealingly coupled to said outer shell, a first valve means coupled to said flexible diaphragm for permitting a one-way flow of air through said first aperture, a back plate having a second aperture and being coupled to said outer shell in a facing relationship with said flexible diaphragm, with a second valve means coupled to said back plate for permitting a one-way flow of air through said second aperture, whereby said flexible diaphragm is deformable to force air through said second aperture and into said space;

a first relief valve mounted to said rigid outer shell and in fluid communication with said space for facilitating a release of air contained in said space;

a wrist strap is attached to said outer shell for encompassing a wrist of said user to secure said therapeutic glove to said user, said wrist strap having hook and loop fasteners secured thereto for securing said wrist strap around said wrist, said wrist strap having an air bladder contained within said wrist strap, said air bladder being selectively inflatable to releasably seal said hand of said user inside said glove;

a second pumping means for injecting air into said air bladder; and, a second relief valve secured to said wrist strap and in fluid communication with said air bladder for facilitating a release of air contained in said air bladder.

* * * * *